US006451943B1

(12) United States Patent
Burkhardt et al.

(10) Patent No.: US 6,451,943 B1
(45) Date of Patent: Sep. 17, 2002

(54) PROCESS FOR THE OXIDATION OF ALCOHOLS USING HOMOGENEOUSLY SOLUBLE POLYMER-ENLARGED NITROGEN COMPOUNDS AS THE CATALYST

(75) Inventors: Olaf Burkhardt, Kalmthout; Jens Woeltinger, Hanau; Andreas Karau, Neustad; Jean-Louis Philippe, Dreieich; Hans Henniges, Bonn, all of (DE); Andreas Bommarius, Atlanta, GA (US); Hans-Peter Krimmer, Dietzenbach; Karlheinz Drauz, Freigericht, both of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/879,985

(22) Filed: Jun. 14, 2001

(30) Foreign Application Priority Data

Jun. 15, 2000 (DE) .......................................... 100 29 597

(51) Int. Cl.$^7$ .............................................. C08F 126/06
(52) U.S. Cl. ........................ 526/265; 526/258; 526/312; 526/328.5; 526/332
(58) Field of Search ................................. 526/258, 265, 526/312, 328.5, 332; C08F 126/06

(56) References Cited

FOREIGN PATENT DOCUMENTS

| DE | 27 48 362 | 5/1979 |
| DE | 199 47 505 | 4/2001 |
| EP | 0 001 803 | 5/1979 |
| WO | WO 98/22415 | 5/1998 |

OTHER PUBLICATIONS

Osa et al. Chem. Lett. (1988), (8), 1423–6.*
MacCorquodale et al. Tetrahedron Lett. (1990), 31(5), 771–4.*
P. L.. Anelli, et al., J. Org. Chem, vol. 52, No. 12, pp. 2559–2562, "Fast and Selective Oxidation of Primary Alcohols to Aldehydes or to Carboxylic Acids and of Secondary Alcohols to Ketones Mediated by Oxoammonium Salts Under Two–Phase Conditions," 1987.
T. Miyazawa, et al., Journal of Polymer Sciences, vol. 23, pp. 2487–2494, "Oxidation of Benzyl Alcohol with FE(III) Using Polymers Containing the Nitroxyl Radical Structure as a Mediator," 1985.

A. E. J. De Nooy, et al., Synthesis, pp. 1153–1174, "On the Use of Stable Organic Nitroxyl Radicals for the Oxidation of Primary and Secondary Alcohols," Oct. 1, 1996.

W. Liang, et al., Polymer Degradation and Stability, vol. 32, No. 1, pp. 39–49,"Effect of Structure of Polymeric Hindered Amines on the Oxidation of Polymers: Part 2–Oxidation of Polypropylene," 1991.

S. Rissom, et al., Tetrahedron: Asymmetry, vol. 10, pp. 923–928, "Asymmetric Reduction of Acetophenone in Membrane Reactors: Comparison of Oxazaborolidine and Alcohol Dehydrogenase Catalysed Processes," 1999.

J. A. Cella, et al., J. Org. Chem., vol. 40, No. 12, pp. 1860–1862, "Nitroxide–Catalyzed Oxidation of Alcohols Using m–Chloroperbenzoic Acid. A New Method," 1975.

T. Mueller, et al., Journal of Molecular Catalysis A: Chemical, vol. 116, pp. 39–42, "Separation of Catalyst Compounds in Two–Phase and Uni–Phase Systems by Membranes," 1997.

G. Bell, et al., Engineering Processes for Bioseparations, pp. 135–165, "Membrane Separation Processes," 1994.

* cited by examiner

*Primary Examiner*—Helen L. Pezzuto
(74) *Attorney, Agent, or Firm*—Oblon, Spivak, McClelland, Maier & Neustadt, P.C.

(57) ABSTRACT

The present invention relates to a process for the oxidation of alcohols using an oxidation agent and catalytic amounts of homogeneously soluble polymer-enlarged nitroxyl derivatives that are obtained by copolymerization of a mixture containing a compound (I)

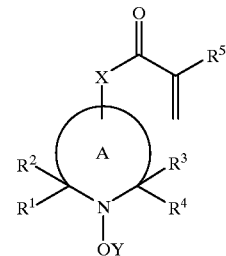

(I)

16 Claims, No Drawings

PROCESS FOR THE OXIDATION OF ALCOHOLS USING HOMOGENEOUSLY SOLUBLE POLYMER-ENLARGED NITROGEN COMPOUNDS AS THE CATALYST

BACKGROUND OF THE INVENTION

1. Field of the Invention

The present invention is directed at a process for the oxidation of alcohols using homogeneously soluble polymer-enlarged nitrogen compounds as catalysts. In particular, the invention relates to a process where the catalysts used are compounds that can be obtained by polymerization of a mixture containing (i): 0.1–100, preferably 1–20 wt. -% of a compound (I)

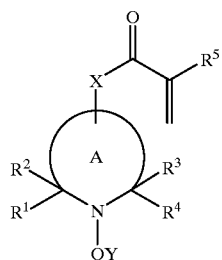

(ii): 0–99.9, preferably 80–99 wt. -% (meth)acrylic acid ester, (iii): 0–80, preferably 1–20 wt. -% other α,β-unsaturated compounds, other than i) wherein A is a ring with 5 to 8 elements, which in addition to one nitrogen can have 0–3 other hetero atoms, such as N, O, S, and which in addition to the substituents shown in the formula can have 0–3 other radicals, such as $(C_1–C_8)$-alkyl, $(C_1–C_8)$-alkoxy, halogens, wherein $R^1$, $R^2$, $R^3$, $R^4$ are, independent of each other, $(C_1–C_8)$-alkyl, $(C_6–C_{18})$-aryl, $(C_7–C_{19})$-aralkyl, $(C_3–C_8)$-cycloalkyl, or $R^1$ and $R^2$ and/or $R^3$ and $R^4$ or $R^1$ and $R^3$ and/or $R^2$ and $R^4$ are connected with one another via a $(C_2–C_8)$-alkylene bridge, wherein $R^5$ is H or methyl, X is O, NH, $NR^1$, and wherein Y is · or H, such as HEMA or EGDMA. It is understood that all subranges and numbers within the above discussed ranges are present as if explicitly written out.

In organic synthesis, the oxidation of alcohols represents an important transformation for obtaining aldehydes, ketones, or acids. These in turn are advantageously suitable, if they are not themselves intended as the target molecule, for further reaction to produce successor products, since they are very easily accessible to nucleophilic addition reactions. They therefore frequently play a key role specifically in the technical production of bioactive molecules, as part of the synthesis path.

The oxidation of secondary and primary alcohols to produce aldehydes and ketones with N-oxygen compounds of 2,2,6,6-tetramethyl-4-piperidine (TEMPO) in the presence of oxidants such as m-CPBA, hypochlorite/bromite solution, or $K_3Fe(CN)_6$ has been known for a long time (J. Org. Chem. 1987, 52, 2559–62; ibid. 1975, 40, 1860; Synthesis 1966, 1153). Furthermore, polymer-enlarged TEMPO radicals already have been synthesized with the purpose of working them into polymer mixtures as UV stabilizers (DE 2748362; L. Wenzhong, Polym. Degra. and Stab. 1991, 31, 353–364).

Endo et al. used partially soluble polymer-enlarged TEMPO compounds in alcohol oxidation reactions, among other substances (Journal of Polymer Science: Polymer Chemistry Edition, Vol. 23, 2487–94 (1985)). However, it was shown that the insoluble oxidation catalysts of the type introduced there were better.

An object of the present invention is to provide a process for the oxidation of alcohols in the presence of oxidation catalysts, on the basis of homogeneously soluble polymer-enlarged nitrogen compounds. In particular, this process is usable on a technical scale, in other words advantageous with regard to the aspects of economics and ecology.

Because an oxidation agent and catalytic amounts of homogeneously soluble polymer-enlarged nitroxyl derivatives are used in a process for the oxidation of alcohols, where these derivatives are obtained by copolymerization of a mixture containing (i): 0.1–100, preferably 1–20 wt. -%, including 3, 5, 10 and 15 wt. % and all weights percent between all stated values of a compound (I)

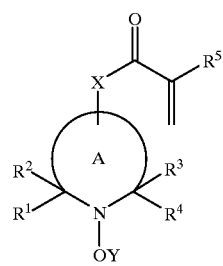

where Y= · or H,

A is a ring with 5 to 8 elements, which in addition to one nitrogen can have 0–3 other hetero atoms, such as N, O, S, and which in addition to the substituents shown in the formula can have 0–3 other radicals, such as $(C_1–C_8)$-alkyl, $(C_1–C_8)$-alkoxy, halogens, $R^1$, $R^2$, $R^3$, $R^4$ are, independent of each other, $(C_1–C_8)$-alkyl, $(C_6–C_{18})$-aryl, $(C_7–C_{19})$-aralkyl, $(C_3–C_8)$-cycloalkyl, or $R^1$ and $R^2$ and/or $R^3$ and $R^4$ or $R^1$ and $R^3$ and/or $R^2$ and $R^4$ are connected with one another via a $(C_2–C_8)$-alkylene bridge, $R^5$ is H or methyl, X is O, NH, $NR^1$, and wherein Y is the 0–3 other radicals or H.

(ii): 0–99.9, including 5, 10, 20, 30, 40, 50, 60, 70, 80, and 90 and all weights percent between all stated values, preferably 80–99 wt. -% (meth)acrylic acid ester, (iii): 0–80, including 5, 10, 20, 30, 40, 50, 60 and 70 and all weights percent between all stated values, preferably 1–20 wt. -% other α,β-unsaturated compounds, such as HEMA or EGDMA, the desired alcohol oxidation products, preferably the aldehydes and ketones, are obtained in a surprisingly simple and cost-effective manner. According to the invention, the oxidation reaction is completed within a few minutes, and the mixture can be processed. The catalyst can be removed and reused, and the yields of oxidation product are almost quantitative. Because the catalyst can be reused, the synthesis costs can be kept low.

It is understood that · signifies a radical electron in the context of this invention.

In a preferred embodiment, the radicals $R^1$–$R^4$=methyl, $R^5$=methyl or H, X=O, NH, where A represents a piperidine ring.

A process where the polymer-enlarged nitroxyl derivative with the formula (II)

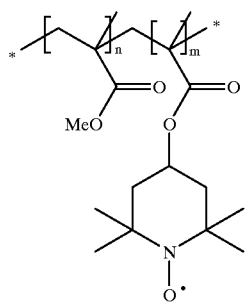

with a ratio of n/m of 1–100, preferably 1–50, and an average molecular weight of 1–200 kDa, preferably 10–100 kDa, is used, is especially preferred.

Other α,β-unsaturated compounds of Type iii that can be used are particularly those monomers that help to change the solubility properties of the polymer, i.e. ideally adapt it to the solvent system to be used. These monomers furthermore can have a crosslinking effect. This has the result that individual polymer strands are connected with one another, which in turn can have a significant influence on the solubility properties and the secondary structure of the polymer backbone and thereby indirectly on the reactivity of the catalyst. Other compounds that can be used are preferably the monomers of component i) and ii) of the polymerizate iii) in DE 19734360. The use of HEMA or EGDMA is very especially preferred in this regard.

In principle, the substances that a person skilled in the art would consider for use for this reaction can be used as oxidation agents. Preferably, these are $K_3Fe(CN)_3$ or aqueous NaOCl solution. Aqueous NaOCl solution is preferred, since it is less expensive and does not result in any cyanide problems, especially on a large technical scale.

The oxidation according to the invention is fundamentally conducted in accordance with that using monomer TEMPO, preferably in a two-phase system of organic and aqueous solvents. Ethyl acetate, acetonitrile, dichloromethane, or benzonitrile can serve as preferred organic solvents. Ethyl acetate and acetonitrile are very especially preferred.

The oxidation agent, the polymer-enlarged nitroxyl derivative of Formula (I), preferably that of Formula (II), is dissolved in the selected two-phase system. In the aqueous phase, the pH is adjusted in such a way that oxidation takes place at a pH of 6–13, preferably 9–10. Preferably, sodium carbonate is used to adjust the pH. However, any of the bases that a person skilled in the art would use for this purpose can be used, such as potassium carbonate, sodium hydrogen carbonate, sodium hydrogen phosphate, for example. Subsequently, the alcohol can be added to the mixture. The reaction is quantitatively completed in a few minutes.

The reaction is preferably carried out at temperatures from −20° C.–80° C., preferably 0–30° C. After completion of the reaction, it can be processed using methods known to a person skilled in the art.

If work is carried out using a two-phase system, the phase that contains organic product and possibly catalyst is separated from the aqueous phase. A special advantage of the process according to the invention is that the polymer-enlarged catalyst can easily be recovered from the organic phase after the reaction is complete, and is therefore available for another oxidation cycle. This can be done using filtration by means of an ultrafiltration/nanofiltration membrane, or by means of precipitation by adding suitable solvents, preferably alcohols such as methanol or ethanol, petroleum ether, hexane, or diethyl ether.

However, the use of the process in a membrane reactor is especially preferred. In this way, the synthesis processes that are normally carried out using the batch process can take place quasi-continuously or continuously, and this appears to be particularly advantageous for a technical process, from a cost aspect. The use of the process according to the invention in a membrane reactor takes place analogous to the process described in the state of the art (T. Mizller, J. Mol. Cat. A: Chem. 1997, 116, 39–42; DE 199 10 691.6; Wandrey et al., Tetrahedron Asymmetry 1999, 10, 923–928). In this connection, the membrane reactor can act as a cross-flow filtration module or a dead-end filtration module (DE 19947505.9 as well as DE 19910691.6 or "Engineering processes for Bioseparations," edited by: Laurence R. Weatherley, pages: 135–165; Butterworth-Heinemann, 1994; ISBN: 0 7506 1936 8).

Another aspect of the invention deals with the use of the oxidation products produced according to the invention in organic synthesis, preferably for the production of bioactive compounds.

The present process allows simple oxidation of alcohols to produce the corresponding desired derivatives, which can be well carried out on a technical scale. In this connection, the reaction times that result are surprisingly short, as compared with the known insoluble polymer-enlarged species. This, and the fact that the catalyst can be easily recycled and reused, are the reasons why the claimed process is very well suited for technical use. Furthermore, excellent selectivity in favor of primary alcohols is found if both primary and secondary alcohols are present in the substrate or in the reaction mixture.

The following are understood to be $(C_1–C_8)$alkyl: methyl, ethyl, n-propyl, isopropyl, n-butyl, isobutyl, sec-butyl, tert-butyl, pentyl, hexyl, heptyl, or octyl, as well as all bond isomers.

A $(C_6–C_{18})$-aryl radical is understood to be an aromatic radical with 6 to 18 C atoms. In particular, this includes compounds such as phenyl, napththyl, anthryl, phenanthryl, biphenyl radicals. These can be substituted with $(C_1–C_8)$-alkoxy, $(C_1–C_8)$-haloalkyl, OH, Cl, $NH_2$, $NO_2$, where single and multiple substitution is possible. In addition, the radical can have one or more hetero atoms such as N, O, S.

$(C_1–C_8)$-alkoxy is a $(C_1–C_8)$-alkyl radical bound to the molecule in question via an oxygen atom.

A $(C_7–C_{19})$-aralkyl radical is a $(C_6–C_{18})$-aryl radical bound via a $(C_1–C_{18})$-alkyl radical.

Within the scope of the invention, the term acrylate is also understood to mean the term methacrylate.

$(C_1–C_8)$-haloalkyl is a $(C_1–C_8)$-alkyl radical substituted with one or more halogen atoms. Chlorine and fluorine are halogen atoms that come into particular consideration. The term $(C_2–C_8)$-alkylene chain is understood to mean a $(C_2–C_8)$-alkyl radical that is bound to the molecule in question via two different C atoms. It can be substituted with $(C_1–C_8)$-alkoxy, $(C_1–C_8)$-haloalkyl, OH, halogen, $NH_2$, $NO_2$, SH, S—$(C_1–C_8)$-alkyl, where single and multiple substitution is possible.

$(C_3–C_8)$-cycloalkyl is understood to mean cyclopropyl, cyclobutyl, cyclopentyl, cyclohexyl, cycloheptyl, or cyclooctyl radicals. Halogen is fluorine, chlorine, bromine, iodine.

Within the scope of the invention, a membrane reactor is understood to mean any reaction container where the catalyst is enclosed in a reactor, while substances with a low molecular weight are passed to the reactor or can leave it. In this connection, the membrane can be directly integrated into the reaction space, or be built into a separate filtration module outside of it, where the reaction solution flows through the filtration module continuously or intermittently, and the retentate is passed into the reactor. Suitable embodiments are described in W098/22415 and in Wandrey et al. in Jahrbuch [Yearbook] 1998, Verfahrenstechnik and Chemieingenieurwesen [Process Technology and Chemical Engineering], VDI p. 151 ff.; Wandrey et al. in Applied Homogeneous Catalysis with Organometallic Compounds, Vol. 2, VCH 1996, p. 832 ff.; Kragl et al., Angew. Chem. 1996, 6, 684 f., among other references.

EXAMPLES

1.1 Polymerization of 4-Methacryloyloxy-2,2,6,6-Tetramethyl Piperidine

Reaction Equation

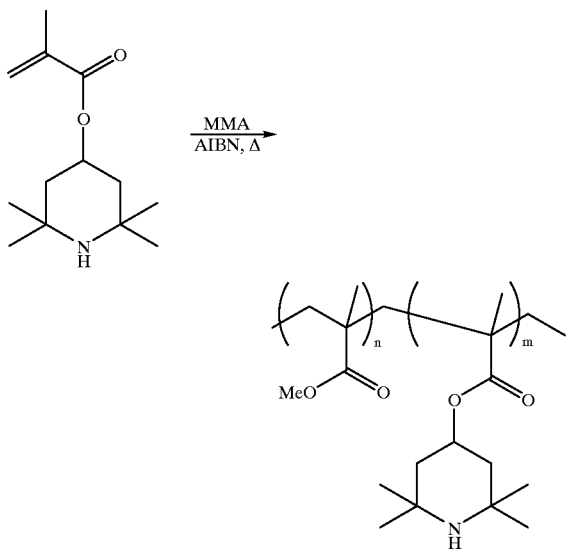

Chemicals
  4-methacryloyloxy-2,2,6,6-tetramethyl piperidine M=225 g/mol: 4.05 g (18 mmol)
  Methyl methacrylate (MMA) M=100. 12 g/mol: 18.02 g (180 mmol)
  2,2'-azo-bis(2-methyl propionitrile) (AIBN) M=164.21 g/mol: 0.325 g (1.98 mmol)
  Isobutyl methyl ketone: 40 ml
  Petroleum ether: 550 ml Implementation 18.02 g MMA, 20 ml isobutyl methyl ketone, 4.05 g 4-methacryloyloxy-2,2,6,6-tetramethyl piperidine, and 0.325 g AIBN are heated to 80° C. in a 100 ml three-neck flask, under nitrogen. The batch is then stirred for 2.5 h at 80° C., then overnight at room temperature, under nitrogen. The viscous reaction mixture is diluted with 20 ml isobutyl methyl ketone, and heated to 80° C.

The warm solution is slowly poured into 500 ml petroleum ether. A white precipitate forms. The suspension is stirred for another 2 h. The precipitate is filtered off, and the filter cake is washed with 50 ml petroleum ether. The product, a white powder, is dried in a vacuum at 40° C. NMR spectra confirm the desired product at a ratio of n/m-10.

Yield: 21.2 g (96.1% of theory)
GPC: Mn=46,000 g/mol Mw=62,000 g/mol

In an analogous experiment with 2 mol-% AIBN, a polymer with Mn=21,250 g/mol and Mw=41,300 g/mol is obtained.

1.2 Reaction of Polymer 4-Methacryloyloxy-2,2,6,6-Tetramethyl Piperidine with Hydrogen Peroxide to Produce the Corresponding 4-Methacryloyloxy-2,2,6,6-Tetramethyl Piperidine-1-Oxyl Reaction Equation

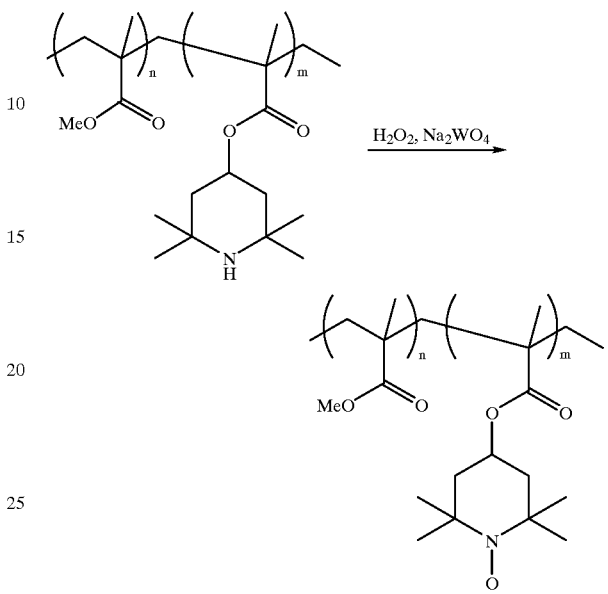

Chemicals
  Polymer 4-methacryloyloxy-2,2,6,6-tetramethyl piperidine (Mn =21,250 g/mol and Mw=41,300 g/mol) M=1,226 g/mol: 10.17 g (8.3 mmol)
  Hydrogen peroxide (30%) M=34 g/mol: 1.36 g (12 mmol)
  Sodium tungstate dihydrate M=329.9 g/mol: 0.016 g (0.05 mmol)
  Ethylene diamine tetraacetic acid M=292.3 g/mol: 0.026 g (0.09 mmol)
  Petroleum ether: 750 ml
  Methanol: 250 ml
  Isobutyl methyl ketone: 50 ml
  Tetrahydrofurane: 50 ml
  VE water: 800 ml Implementation 10.17 g polymer 4-methacryloyloxy-2,2,6,6-tetramethyl piperidine, 0.026 g ethylene diamine tetraacetic acid, and 0.016 g sodium tungstate dehydrate are dissolved in a mixture of 250 ml methanol and 50 ml isobutyl methyl ketone in a 500 ml three-neck flask. While stirring 1.36 g hydrogen peroxide (30%) are slowly added. Stirring continues for 3 days at room temperature. Subsequently, approximately 200 ml solvent are distilled off, using the rotation evaporator, at 40° C./400 mbar. The residue (yellow-orange) is dripped into 700 ml petroleum ether (cooled to 5° C.). Stirring continues for 2 h at 0° C.–5° C., causing a sticky residue to form. The sticky residue is allowed to settle, and the petroleum ether on top is decanted off. The residue is dissolved in 50 ml tetrahydrofurane and dripped into 700 ml VE water at room temperature —a white precipitate forms. The suspension is stirred overnight, then filtered off, and the filter cake is washed with 100 ml VE water. The product, a pink powder, is dried in a vacuum at 40° C. NMR and UV confirm the desired structure.

Yield: 9.7 g (94.2% of theory)
GPC: Mn 19,350 g/mol Mw=41,100 g/mol

A batch produced in analogous-manner, with a higher polymer educt (Mn=46,000 g/mol and Mw=62,000 g/mol)

1.3 Oxidation of 1-Hexanol to Produce Hexanal, in the Presence of Polymer 4-Ethacryloyloxy-2,2,6,6-Tetramethyl Piperidine-Loxyl Reaction Equation

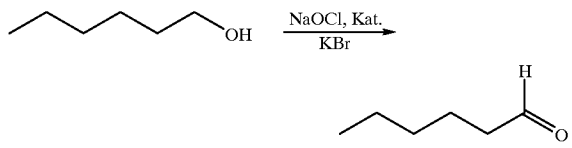

Chemicals

Polymer 4-methacryloyloxy-2,2,6,6-tetramethylpiperidine-1-oxyl (Mn=40,250 g/mol and Mw=63,750 g/mol) M=1,241 g/mol: 0.62 g (0.5 mmol)

1-hexanol M=102.18 g/mol: 5.11 g (50 mmol)

Sodium hypochlorite solution (7.49°s NaOCl) M=74.44 g/mol: 54.61 g (55 mmol) (adjust to pH 9.5 using solid sodium hydrogen carbonate)

Potassium bromide solution (0.5 M) M=119.01 g/mol: 10 ml (5 mmol)

Sodium thiosulfate solution (10%): 125 ml

Dichloromethane: 80 ml

Implementation 0.62 g polymer 4-methacryloyloxy-2,2,6,6-tetramethyl piperidine-loxyl, 5.11 g 1-hexanol, 20 ml dichloromethane, and 10 ml 0.5 M potassium bromide solution are presented in a 100 ml three-neck flask and cooled to −10° C. 54.61 g sodium hypochlorite solution (7.49% NaOCl, adjusted to pH 9.5 with solid sodium hydrogen carbonate) are dripped in within 20 minutes. The reaction is exothermic, and the reaction temperature is kept between 0° C. and 5° C. by means of cooling. Stirring takes place for another 10 minutes at 0° C.–5° C. The aqueous phase is separated off in a separation funnel and shaken out three times, with 20 ml dichloromethane each time. The organic phases are combined and washed two times, with 25 ml sodium thiosulfate solution each time, and once with 75 ml sodium thiosulfate solution (10%). The organic phase is dried using magnesium sulfate. The magnesium sulfate is removed again using filtration. The filtrate is evaporated in a rotation evaporator, at 35° C.–40° C./400 mbar. The crude product obtained is analyzed directly.

NMR analysis confirms the desired product and does not show any indication of remaining alcohol or acids.

Yield: 4.64 g=72.8% of theory

1.4 Oxidation of 2-Hexanol to Produce 2-Hexanone in the Presence of 4-Methacryloyloxy-2,2,6,6-Tetramethylpiperidine-Loxyl Reaction Equation

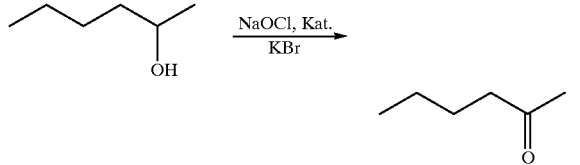

Chemicals

Polymer 4-methacryloyloxy-2,2,6,6-tetramethylpiperidine-1-oxyl (Mn=40,250 g/mol and Mw=63,750 g/mol) M=1,241 g/mol: 0.62 g (0.5 mmol)

2-hexanol M=102.18 g/mol: 5.11 g (50 mmol)

Sodium hypochlorite solution (7.49% NaOCl) M=74.44 g/mol: 54.61 g (55 mmol) (adjust to pH 9.5 using solid sodium hydrogen carbonate)

Potassium bromide solution (0.5 M) M=119.01 g/mol: 10 ml (5 mmol)

Sodium thiosulfate solution (10%): 125 ml

Dichloromethane: 80 ml

Implementation 0.62 g polymer 4-methacryloyloxy-2,2,6,6-tetramethyl piperidine-loxyl, 5.11 g 2-hexanol, 20 ml dichloromethane, and 10 ml 0.5 M potassium bromide solution are presented in a 100 ml three-neck flask and cooled to −10° C. 54.61 g sodium hypochlorite solution (7.49% NaOCl, adjusted to pH 9.5 with solid sodium hydrogen carbonate) are dripped in within 20 minutes. The reaction is exothermic, and the reaction temperature is kept between 0° C. and 5° C. by means of cooling. Stirring takes place for another 10 minutes at 0° C.–5° C. The aqueous phase is separated off in a separation funnel and shaken out three times, with 20 ml dichloromethane each time. The organic phases are combined and washed two times, with 25 ml sodium thiosulfate solution each time, and once with 75 ml sodium thiosulfate solution (10%). The organic phase is dried using magnesium sulfate. The magnesium sulfate is removed again using filtration. The filtrate is evaporated in a rotation evaporator, at 35° C.–40° C./400 mbar. The crude product obtained is analyzed directly.

NMR analysis confirms the desired product and does not show any indication of remaining alcohol or acids.

Yield: 4.58 g=81.8% of theory

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 100 29 597.5, filed on Jun. 15, 2000, which is incorporated herein by reference.

What is claimed is:

1. A process comprising the oxidation of an alcohol in the presence of an oxidation agent and a homogeneously soluble polymer enlarged nitroxyl derivative prepared by copolymerizing i) 0.1–100 wt. % of compound (I)

ii) 0–99.9 wt. % (meth)acrylic acid ester, and iii) 0–80 wt. % α,β-unsaturated compounds other than i)
    wherein A is a ring with 5 to 8 elements, which in addition to one nitrogen can have 0–3 other hetero atoms, such as N, O, S, and which in addition to the substituents shown in the formula can have 0–3 other radicals, such as ($C_1$–$C_8$)-alkyl, ($C_1$–$C_8$)-alkoxy, halogens,

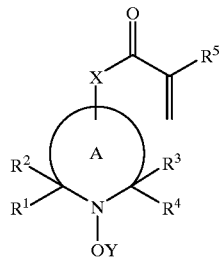

(I)

wherein $R^1$, $R^2$, $R^3$, $R^4$ are, independent of each other, $(C_1-C_8)$-alkyl, $(C_6-C_{18})$-aryl, $(C_7-C_{19})$-aralkyl, $(C_3-C_8)$-cycloalkyl, or $R^1$ and $R^2$ and/or $R^3$ and $R^4$ or $R^1$ and $R^3$ and/or $R^2$ and $R^4$ are connected with one another via a $(C_2-C_8)$-alkylene bridge, wherein $R^5$ is H or methyl, X is O, NH, $NR^1$, and wherein Y is · or H.

2. The process according to claim 1, wherein the polymer-enlarged nitroxyl derivative corresponds to the formula (II)

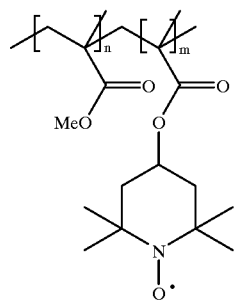

with a ratio of n/m of 1–100 and an average molecular weight of 1–200 kDa.

3. The process according to claim 1, wherein the polymer-enlarged nitroxyl derivative corresponds to the formula (II)

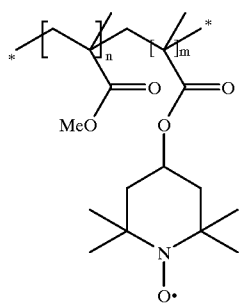

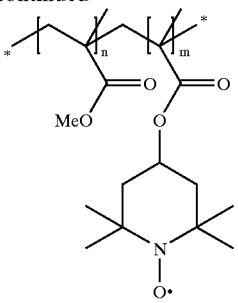

with a ratio of n/m of 1–100 and an average molecular weight of preferably 10–100 kDa.

4. The process according to claim 1, wherein NaOCl solution is used as the oxidation agent.

5. The process according to claim 1, wherein oxidation is carried out at temperatures from −20° C.–80° C.

6. The process according to claim 1, wherein oxidation is carried out at temperatures from 0–30° C.

7. The process according to claim 1, wherein oxidation is carried out at a pH of 6–13.

8. The process according to claim 1, wherein oxidation is carried out at a pH of 9–10.

9. The process according to claim 1, wherein the reaction is carried out continuously, in a membrane reactor.

10. The process according to claim 1, further comprising reusing said copolymer for oxidation of alcohol.

11. The process according to claim 1, wherein the (meth) acrylic acid ester is present in an amount of from 80–99 wt. %.

12. The process according to claim 1, wherein the α,β-unsaturated compounds other than i) are present in an amount from 1–20 wt. %.

13. The process according to claim 1, wherein the α,β-unsaturated compound is HEMA.

14. The process according to claim 1, wherein the α,β-unsaturated compound is EGDMA.

15. The process according to claim 1, wherein at least one of a primary alcohol and a secondary alcohol is available for oxidation.

16. The process according to claim 1, wherein a primary alcohol and a secondary alcohol is available for oxidation.

* * * * *